(12) United States Patent
McLaughlin

(10) Patent No.: US 11,305,333 B2
(45) Date of Patent: Apr. 19, 2022

(54) METHODS FOR FORMING LOW STRESS COMPONENT FOR MEDICAL DEVICES

(71) Applicant: INSULET CORPORATION, Acton, MA (US)

(72) Inventor: Ian McLaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 105 days.

(21) Appl. No.: 16/836,356

(22) Filed: Mar. 31, 2020

(65) Prior Publication Data

US 2021/0299739 A1 Sep. 30, 2021

(51) Int. Cl.
*B21K 1/20* (2006.01)

(52) U.S. Cl.
CPC ..................... *B21K 1/20* (2013.01)

(58) Field of Classification Search
CPC .......... A61M 39/00; B21K 1/20; B23P 15/00; B23P 11/02; B23P 11/025; G01N 15/1218; C21D 6/02; C21D 6/00
See application file for complete search history.

(56) References Cited

U.S. PATENT DOCUMENTS

| 1,441,508 | A | | 1/1923 | Marius |
| 3,579,805 | A | * | 5/1971 | Kast ..................... B23P 11/025 148/529 |
| 5,232,668 | A | | 8/1993 | Grant et al. |
| 5,995,236 | A | | 11/1999 | Roth et al. |
| 6,200,293 | B1 | | 3/2001 | Kriesel et al. |
| 6,514,460 | B1 | | 2/2003 | Fendrock |
| 6,740,059 | B2 | | 5/2004 | Flaherty |
| 6,768,425 | B2 | | 7/2004 | Flaherty et al. |
| 7,137,964 | B2 | | 11/2006 | Flaherty |
| 7,303,549 | B2 | | 12/2007 | Flaherty et al. |
| 7,731,900 | B2 | | 6/2010 | Haar et al. |
| 7,842,241 | B2 | | 11/2010 | Arbogast et al. |
| 7,846,385 | B2 | | 12/2010 | Arbogast et al. |
| 7,846,386 | B2 | | 12/2010 | Arbogast et al. |
| 7,846,387 | B2 | | 12/2010 | Arbogast et al. |
| 7,846,388 | B2 | | 12/2010 | Arbogast et al. |
| 7,867,446 | B2 | | 1/2011 | Arbogast et al. |
| 7,897,107 | B2 | | 3/2011 | Arbogast et al. |

(Continued)

FOREIGN PATENT DOCUMENTS

| EP | 3000497 A2 | 3/2016 |
| EP | 3135965 A1 | 3/2017 |

(Continued)

OTHER PUBLICATIONS

International Preliminary Report on Patentability for the International Patent Application No. PCT/US2019/042160, dated Jan. 28, 2021, 12 pages.

(Continued)

*Primary Examiner* — Lee A Holly
(74) *Attorney, Agent, or Firm* — Goodwin Procter LLP

(57) ABSTRACT

Disclosed herein are approaches of forming a component, such as a valve, for a medical device. One approach includes providing a cylinder within a tube, the tube and the cylinder joined together in an interference fit, and annealing the tube and the cylinder, wherein the tube and the cylinder are no longer joined together in the interference fit following the annealing.

20 Claims, 5 Drawing Sheets

200

201
Providing a Cylinder within a Tube, the Tube and the Cylinder Joined Together in an Interference Fit 203
Annealing the Tube and the Cylinder, Wherein the Tube and the Cylinder are no Longer Joined Together in the Interference Fit Following the Annealing

(56) References Cited

U.S. PATENT DOCUMENTS

| | | |
|---|---|---|
| 7,914,742 B2 | 3/2011 | Arbogast et al. |
| 8,080,205 B2 | 12/2011 | Arbogast et al. |
| D674,400 S | 1/2013 | Fong et al. |
| D677,675 S | 3/2013 | Rampson et al. |
| 8,431,408 B2 | 4/2013 | Lewis et al. |
| D685,083 S | 6/2013 | Schneider et al. |
| 8,465,977 B2 | 6/2013 | Joseph et al. |
| D687,141 S | 7/2013 | Schneider et al. |
| D687,536 S | 8/2013 | Guarraia et al. |
| D688,681 S | 8/2013 | Talbot et al. |
| D692,552 S | 10/2013 | Lovell et al. |
| D703,690 S | 4/2014 | MacCubbin et al. |
| 8,765,482 B2 | 7/2014 | Joseph et al. |
| D713,854 S | 9/2014 | Cojuangco et al. |
| D714,335 S | 9/2014 | Cojuangco et al. |
| 8,894,262 B2 | 11/2014 | Celentano et al. |
| D733,740 S | 7/2015 | Lee et al. |
| D741,871 S | 10/2015 | Chung et al. |
| D745,142 S | 12/2015 | OConnor et al. |
| D748,664 S | 2/2016 | Noack et al. |
| D752,607 S | 3/2016 | Zhang et al. |
| D754,181 S | 4/2016 | Dong et al. |
| D760,272 S | 6/2016 | Li |
| D762,702 S | 8/2016 | Hoang et al. |
| D764,507 S | 8/2016 | Gansca et al. |
| D766,264 S | 9/2016 | Kahn et al. |
| D768,188 S | 10/2016 | Li et al. |
| D774,640 S | 12/2016 | Tyce et al. |
| D776,262 S | 1/2017 | Tyce et al. |
| D776,264 S | 1/2017 | Tyce et al. |
| D776,265 S | 1/2017 | Tyce et al. |
| D779,523 S | 2/2017 | Jensen et al. |
| D779,526 S | 2/2017 | Volovik |
| 9,572,926 B2 | 2/2017 | Cabiri |
| D781,302 S | 3/2017 | Baguley et al. |
| D784,395 S | 4/2017 | Laing et al. |
| D791,813 S | 7/2017 | Kisielius et al. |
| D794,776 S | 8/2017 | Tyce et al. |
| D795,272 S | 8/2017 | Laing et al. |
| D802,011 S | 11/2017 | Friedman et al. |
| D804,019 S | 11/2017 | Costello et al. |
| 9,814,832 B2 | 11/2017 | Agard et al. |
| D804,650 S | 12/2017 | Costello et al. |
| D805,186 S | 12/2017 | Costello et al. |
| D805,187 S | 12/2017 | Costello et al. |
| D805,188 S | 12/2017 | Costello et al. |
| D805,189 S | 12/2017 | Costello et al. |
| D805,190 S | 12/2017 | Costello et al. |
| D807,389 S | 1/2018 | Miller et al. |
| D810,122 S | 2/2018 | McClellan |
| D810,278 S | 2/2018 | Cabiri et al. |
| D813,380 S | 3/2018 | Stonecipher et al. |
| D816,092 S | 4/2018 | Mazur et al. |
| D816,698 S | 5/2018 | Oldenburger et al. |
| D817,481 S | 5/2018 | Cabiri et al. |
| D817,977 S | 5/2018 | Kato et al. |
| D822,692 S | 7/2018 | Loychik et al. |
| D824,933 S | 8/2018 | Harris et al. |
| D826,239 S | 8/2018 | Duriseti et al. |
| D826,956 S | 8/2018 | Pillalamarri et al. |
| D829,229 S | 9/2018 | Durkan et al. |
| D830,407 S | 10/2018 | Kisielius et al. |
| D831,034 S | 10/2018 | Hoang et al. |
| D833,461 S | 11/2018 | Dieken et al. |
| D834,061 S | 11/2018 | Wall et al. |
| D834,610 S | 11/2018 | Kim |
| D835,116 S | 12/2018 | Taylor et al. |
| D835,631 S | 12/2018 | Yepez et al. |
| D835,663 S | 12/2018 | Ho et al. |
| D836,770 S | 12/2018 | Nazzaro et al. |
| D837,240 S | 1/2019 | Van Tricht |
| D838,359 S | 1/2019 | Boyaval et al. |
| D838,840 S | 1/2019 | Cabiri et al. |
| D839,284 S | 1/2019 | Pillalamarri et al. |
| D840,420 S | 2/2019 | Chalker et al. |
| D840,421 S | 2/2019 | Chalker et al. |
| D840,531 S | 2/2019 | Guillermo et al. |
| D841,023 S | 2/2019 | Millett |
| D844,652 S | 4/2019 | Edman |
| D845,991 S | 4/2019 | Kessler et al. |
| D847,154 S | 4/2019 | Cheney et al. |
| D847,852 S | 5/2019 | Sapre |
| D848,460 S | 5/2019 | Wiese et al. |
| D849,767 S | 5/2019 | Mok et al. |
| D851,666 S | 6/2019 | Lu et al. |
| D851,752 S | 6/2019 | Nazzaro et al. |
| D853,416 S | 7/2019 | Ryan et al. |
| D853,426 S | 7/2019 | Alexander |
| D853,427 S | 7/2019 | Alexander |
| D854,559 S | 7/2019 | Dudey |
| D856,506 S | 8/2019 | Wu et al. |
| 2004/0116847 A1 | 6/2004 | Wall |
| 2005/0009126 A1 | 1/2005 | Andrews et al. |
| 2005/0125162 A1 | 6/2005 | Hajizadeh et al. |
| 2005/0201897 A1 | 9/2005 | Zimmer et al. |
| 2005/0232815 A1 | 10/2005 | Ruhl et al. |
| 2005/0238507 A1 | 10/2005 | Dilanni et al. |
| 2009/0254041 A1 | 10/2009 | Krag et al. |
| 2010/0152658 A1 | 6/2010 | Hanson et al. |
| 2010/0168683 A1 | 7/2010 | Cabiri |
| 2010/0317951 A1 | 12/2010 | Rutkowski et al. |
| 2011/0193704 A1 | 8/2011 | Harper et al. |
| 2011/0218495 A1 | 9/2011 | Remde |
| 2011/0289497 A1 | 11/2011 | Kiaie et al. |
| 2012/0095316 A1 | 4/2012 | Lewis et al. |
| 2012/0201048 A1 | 8/2012 | Prais |
| 2013/0204130 A1 | 8/2013 | Mcarthur et al. |
| 2014/0012119 A1 | 1/2014 | Geaghan et al. |
| 2014/0054883 A1 | 2/2014 | Lanigan et al. |
| 2014/0074033 A1 | 3/2014 | Sonderegger et al. |
| 2014/0078263 A1 | 3/2014 | Kim |
| 2014/0131199 A1 | 5/2014 | Simmons et al. |
| 2014/0254170 A1 | 9/2014 | Celentano et al. |
| 2014/0296787 A1 | 10/2014 | Agard et al. |
| 2014/0316379 A1 | 10/2014 | Sonderegger et al. |
| 2015/0283335 A1 | 10/2015 | Lin |
| 2015/0338349 A1 | 11/2015 | Carter et al. |
| 2015/0361154 A1 | 12/2015 | Jowett et al. |
| 2016/0015891 A1 | 1/2016 | Papiorek |
| 2016/0038689 A1 | 2/2016 | Lee et al. |
| 2016/0058941 A1 | 3/2016 | Wu et al. |
| 2016/0135747 A1 | 5/2016 | Frey et al. |
| 2016/0310665 A1 | 10/2016 | Hwang et al. |
| 2017/0028132 A1 | 2/2017 | Cronenberg et al. |
| 2017/0106138 A1 | 4/2017 | Cabiri |
| 2017/0214584 A1 | 7/2017 | Kanojia et al. |
| 2017/0234858 A1 | 8/2017 | Depa et al. |
| 2017/0354785 A1 | 12/2017 | Gazeley et al. |
| 2018/0207357 A1 | 7/2018 | John |
| 2018/0236173 A1 | 8/2018 | Mccaffrey et al. |
| 2018/0256815 A1 | 9/2018 | Nazzaro |
| 2019/0022317 A1 | 1/2019 | Uddin et al. |
| 2019/0091404 A1 | 3/2019 | Nazzaro et al. |
| 2019/0167895 A1 | 6/2019 | Dechellette et al. |
| 2019/0240417 A1 | 8/2019 | Hostettler et al. |
| 2020/0197605 A1 | 6/2020 | Haidar |

FOREIGN PATENT DOCUMENTS

| | | |
|---|---|---|
| FR | 2096275 A5 | 2/1972 |
| GB | 357139 A | 9/1931 |
| GB | 810488 A | 3/1959 |
| WO | 2007092618 A2 | 8/2007 |

OTHER PUBLICATIONS

International Search Report and Written Opinion for the International Patent Application No. PCT/US2021/047695, dated Jan. 31, 2022, 26 pages.

\* cited by examiner

200

201
Providing a Cylinder within a Tube, the Tube and the Cylinder Joined Together in an Interference Fit 203
Annealing the Tube and the Cylinder, Wherein the Tube and the Cylinder are no Longer Joined Together in the Interference Fit Following the Annealing

FIG. 5

METHODS FOR FORMING LOW STRESS COMPONENT FOR MEDICAL DEVICES

FIELD

Embodiments herein generally relate to medication delivery. More particularly, embodiments herein relate to wearable drug delivery devices and methods for forming low stress components of wearable drug delivery devices.

BACKGROUND

Many wearable drug delivery devices include valves for controlling flow of fluids (e.g., insulin) therein. Current-art rubberless valves require a high force due to a relatively wide range of interference. Meanwhile, precision made valves may be formed by machining or grinding to very tight tolerances to reduce the interference. Neither of these current designs meets the needs of a small, low cost, on body device, as it is not feasible to be able to generate the forces needed to move available low cost rubberless valves, and it is not feasible to add the cost of precision-made parts. Accordingly, there is a need to create low force valves without using rubber seals or requiring tight part tolerances.

SUMMARY

In one approach of the disclosure, a method of forming a valve for a medical device may include providing a cylinder within a tube, the tube and the cylinder joined together in an interference fit, and annealing the tube and the cylinder, wherein the tube and the cylinder are no longer joined together in the interference fit following the annealing.

In another approach of the disclosure, a method of forming a valve for a wearable medical device may include providing a cylinder within a tube, the tube and the cylinder joined together in an interference fit, annealing the tube and the cylinder, and cooling the tube and the cylinder after the annealing until the cylinder and the tube are no longer engaged in the interference fit.

In yet another approach of the disclosure, a method of forming a device for a wearable drug delivery system may include joining together a first component within an interior of a second component, wherein the first and second components are engaged together in an interference fit, annealing the first and second components, and cooling the first and second components after the annealing until the first and second components are no longer engaged together in the interference fit.

BRIEF DESCRIPTION OF DRAWINGS

The accompanying drawings illustrate example approaches of the disclosure, including the practical application of the principles thereof, as follows:

FIG. 5 is a process flow for forming the component of FIG. 1 according to embodiments of the present disclosure.

Figure 1:
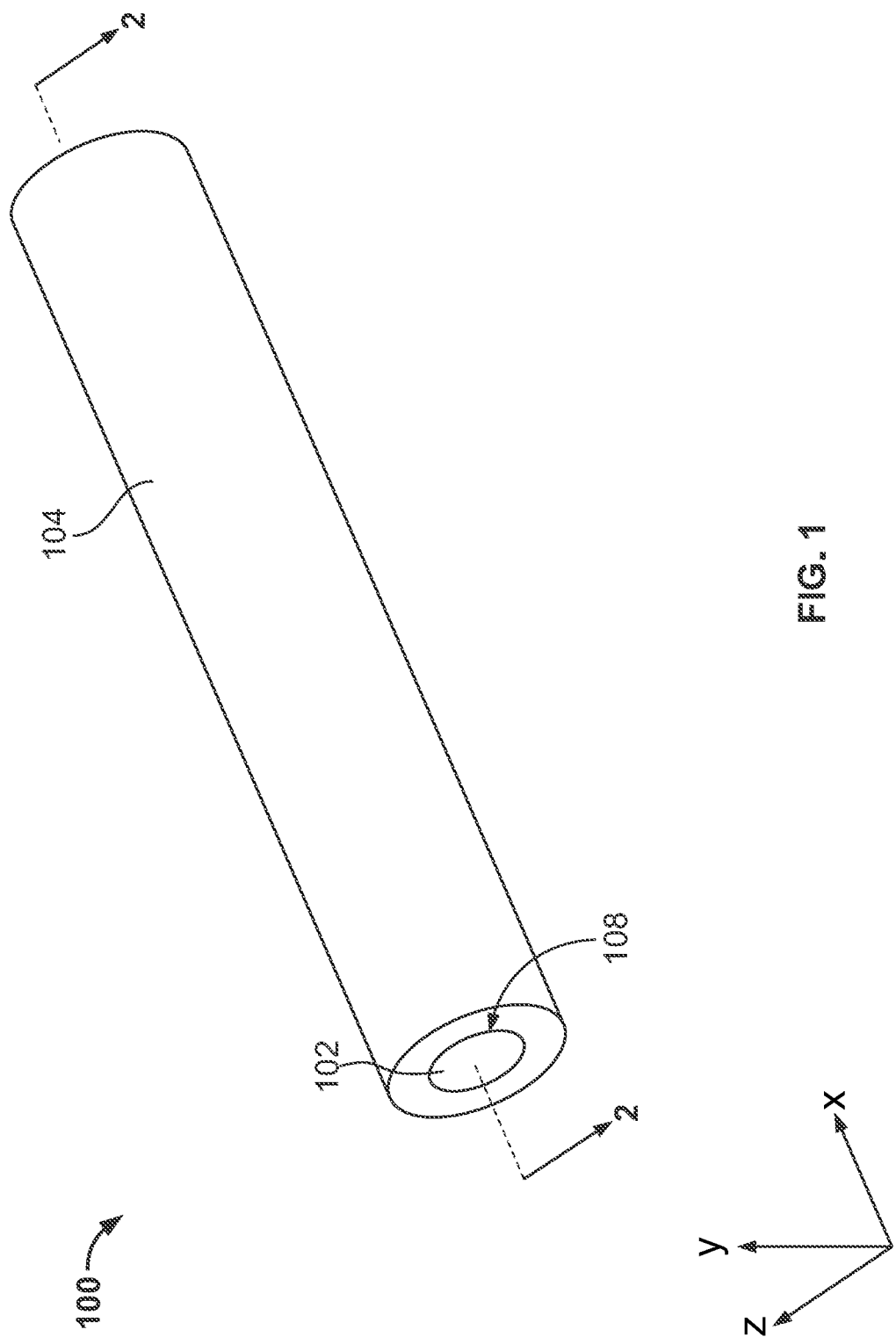
FIG. 1 illustrates a perspective view of a component of a wearable drug delivery device according to embodiments of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, some reference numbers may be omitted in certain drawings.

DETAILED DESCRIPTION

Various approaches in accordance with the present disclosure will now be described more fully hereinafter with reference to the accompanying drawings, where embodiments of the methods are shown. The approaches may be embodied in many different forms and are not to be construed as being limited to the embodiments set forth herein. Instead, these embodiments are provided so this disclosure will be thorough and complete, and will fully convey the scope of the approaches to those skilled in the art.

Examples disclosed herein provide methods for creating a low-force component, such as a valve for a wearable medical device, without using rubber seals or requiring tight part tolerances. Without the need to account for rubber seals, the size of the valves can be reduced without requiring tight part tolerances. As a result, the methods provided herein provide cost savings over conventional methods.

As will be described further herein, two or more parts of the valve (e.g., a tube and cylinder) may be initially assembled in an interference fit that creates a seal. The valve may then be annealed to relieve stress in the individual parts, which may be in tension and/or compression with respect to one another. The annealing process effectively resizes the individual parts such that after cooling they are no longer in interference, and thus are able to move with lower force. Although described herein with respect to an exemplary valve, it will be appreciated that the methods of the present disclosure are applicable to the manufacture of various other small, low cost components suitable for inclusion in a wearable medical device, such as an insulin delivery device.

FIG. 1 illustrates a device or component 100 suitable for inclusion in a wearable drug delivery system according to embodiments of the present disclosure. As shown, the component 100 may be a valve including a cylinder 102 surrounded by a tube 104. During assembly, the tube 104 may be pressed over an exterior of the cylinder 102, which causes the tube 104 to be stressed in tension and the cylinder 102 to be stressed in compression. Once assembled, the cylinder 102 and the tube 104 may be engaged with one another in an interference fit (also referred to as a press fit or friction fit) at an interface 108. Although non-limiting, the cylinder 102 and the tube 104 may be the same or different materials, as will be described in greater detail below.

Figure 2:
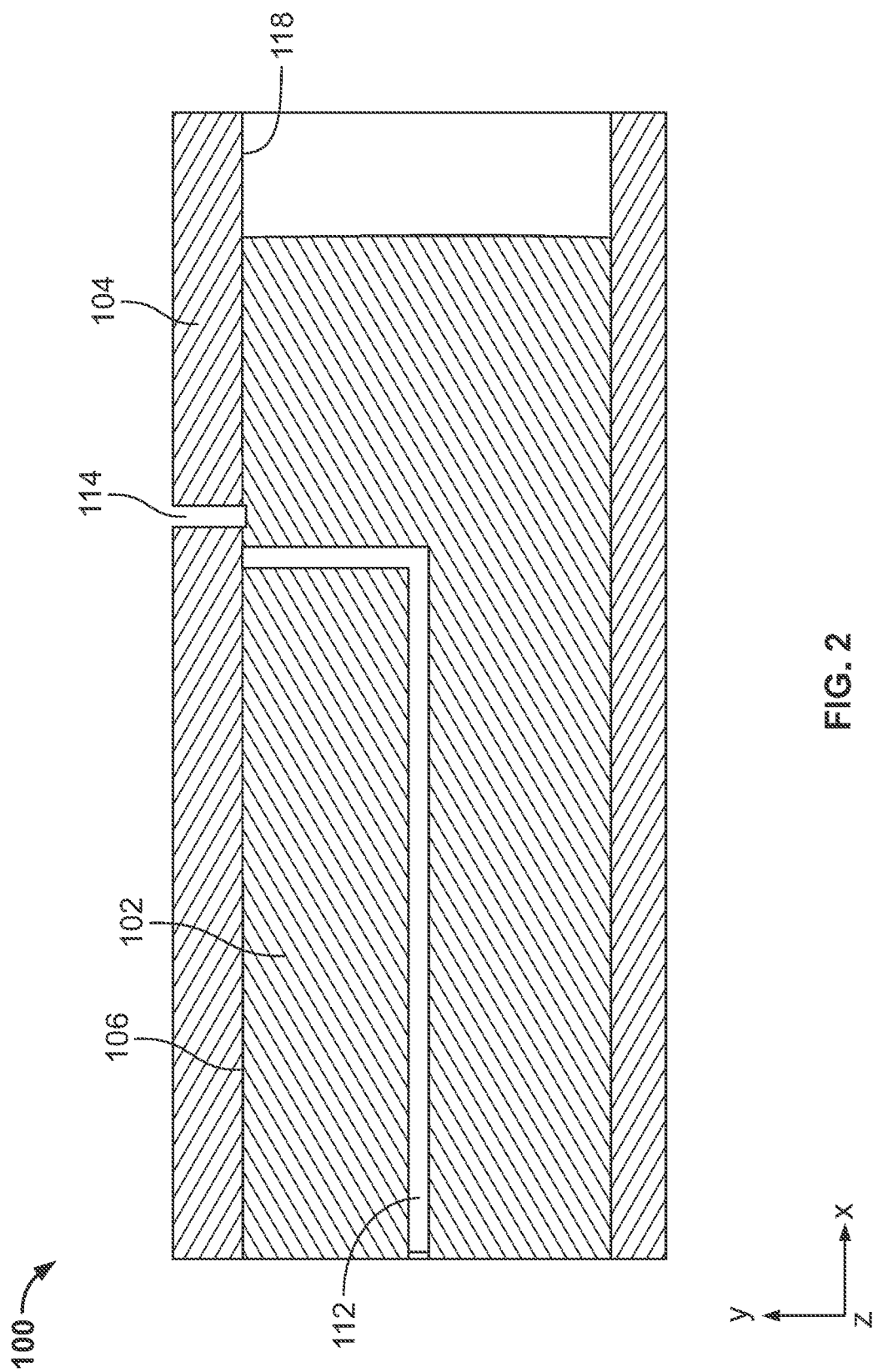
FIG. 2 is a side cross-sectional view of the component of FIG. 1 according to embodiments of the present disclosure.

As shown in FIG. 2, the cylinder 102 may include a central port 112 extending therethrough, while the tube 104 may include an exterior port 114 extending therethrough. In the configuration of FIG. 2, the central port 112 is not aligned with the exterior port 114. However, biasing the cylinder 102 axially (e.g., along the positive x-direction), may bring the central port 112 into alignment with the exterior port 114, thus enabling a fluid to flow through the component 100. In other embodiments, the cylinder 102 and/or the tube 104 may rotate with respect to one another to bring the central port 112 and the exterior port 114 into or out of alignment. An exterior surface 106 of the cylinder 102 and/or an interior surface 118 of the tube 104 may include one or more stopping features (not shown) to limit axial movement of the cylinder 102 and the tube 104 relative to one another.

Figure 3:
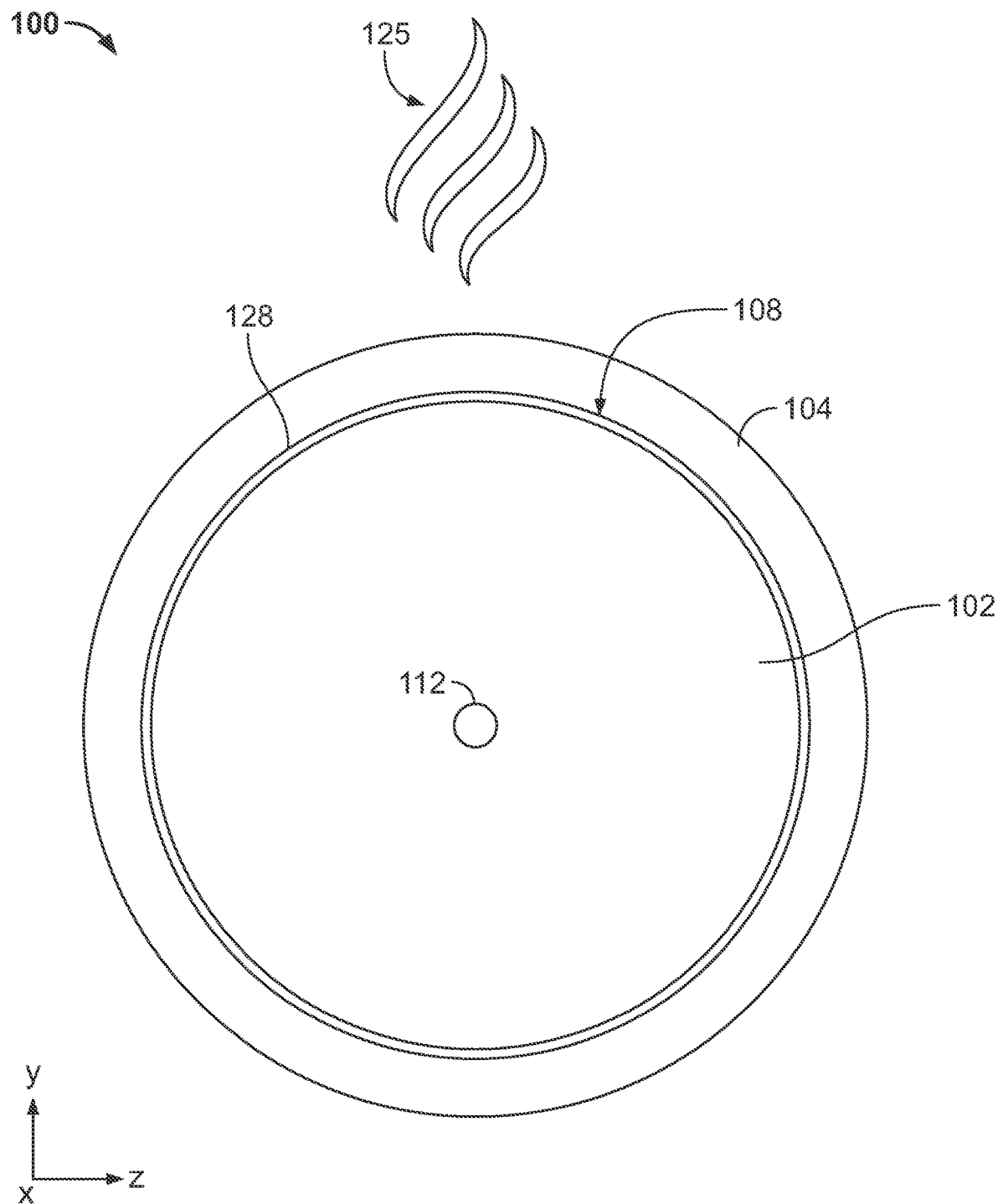
FIG. 3 is an end view of the component of FIG. 1 according to embodiments of the present disclosure.

As demonstrated in FIG. 3, the component 100 may be subjected to an annealing process 125, which relieves stress present in the cylinder 102 and/or the tube 104. The annealing process 125 effectively resizes the component 100 such that after cooling the cylinder 102 and the tube 104 are no longer in interference at the interface 108, and thus are able to move relative to one another with relatively lower force. In some embodiments, an oil 128 (e.g., non-water-soluble silicone) or grease may be provided between the cylinder 102 and the tube 104 to further reduce the forces (e.g., frictional) at the interface 108.

Figure 4:
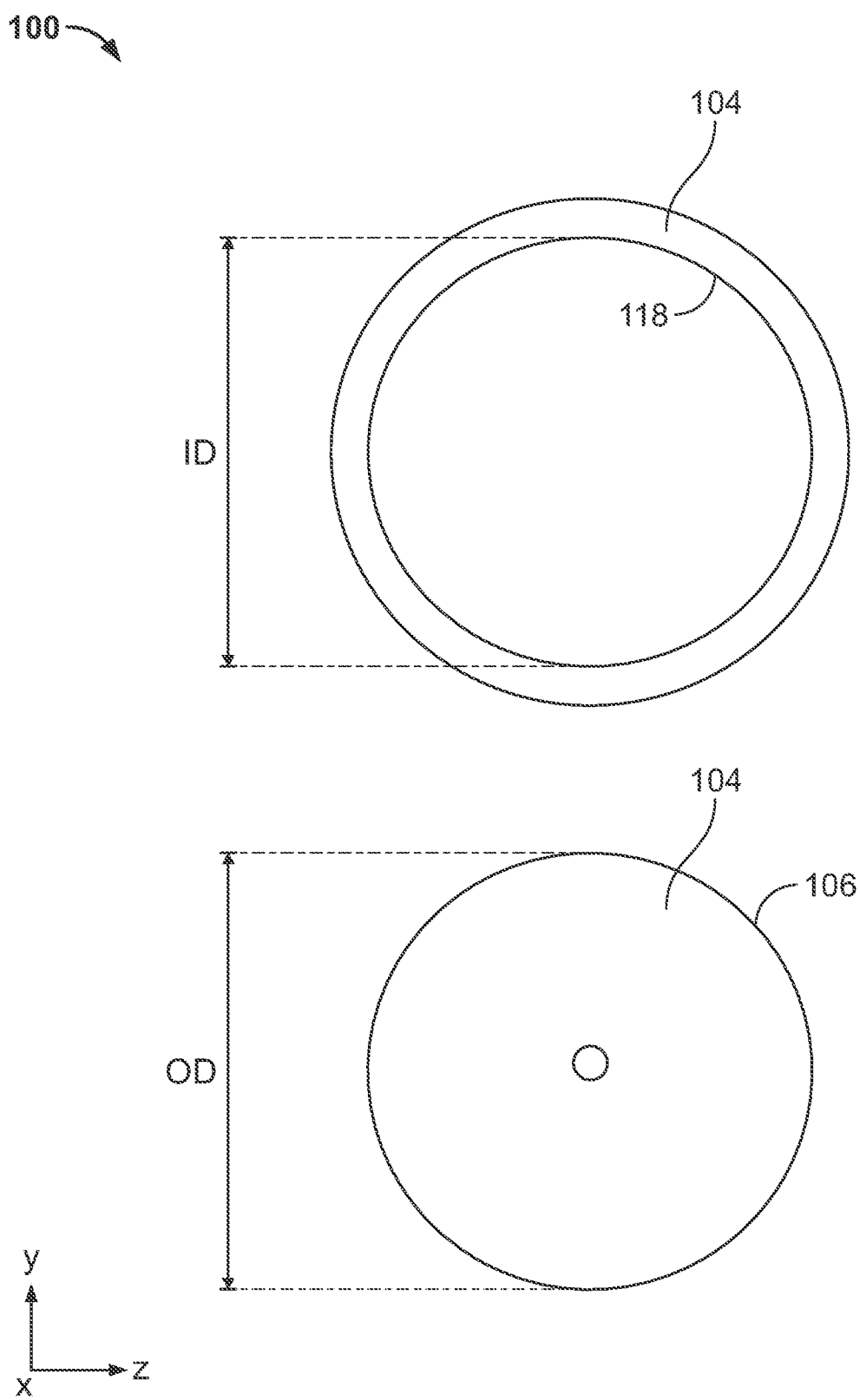
FIG. 4 demonstrates dimensions of the component of FIG. 1 following an annealing process according to embodiments of the present disclosure.

After annealing, as demonstrated in FIG. 4, the inside diameter "ID" of the interior surface 118 of the tube 104 is approximately equal to the outside diameter "OD" of the exterior surface 106 of the cylinder 102. Prior to annealing, OD>ID, resulting in the interference fit. With the tube 104 and the cylinder 102 now in a "line-to-line" fit, the tube 104 and the cylinder 102 may move axially and/or rotationally with respect to one another.

It will be appreciated that material selection for the cylinder 102 and the tube 104 influences how the component 100 is ultimately configured following annealing. Materials may be selected to account for the thermal expansion of the cylinder 102 and/or tube 104. For example, if the cylinder 102 and the tube 104 are made of a same plastic (or any combination of materials having a same coefficient of thermal expansion), the interference fit will be eliminated following annealing. More specifically, the cylinder 102 and tube 104 may initially thermally expand a same amount, thus maintaining the interference and stressed condition. Annealing the cylinder 102 and the tube 104 will remove this stress. Once the cylinder 102 and the tube 104 cool, the cylinder 102 and the tube 104 shrink the same amount. After processing, the cylinder 102 and the tube 104 can be disassembled and the tube 104 will remain in its stretched configuration because of the annealing process. With the interference removed, the cylinder 102 and the tube 104 may move freely relative to one another.

In another example in which the cylinder 102 is made of a plastic and the tube 104 is made of a metal, the annealed plastic of the cylinder 102 expands greater than the metal of the tube 104. However, the metal tube 104 keeps the plastic cylinder 102 from expanding radially, increasing the interference. Therefore, after annealing, the plastic cylinder 102 elongates and the diameter of the plastic cylinder 102 is reduced to match the ID of the metal tube 104. Once complete, the plastic cylinder 102 will have become smaller and the interference removed so the parts may move freely.

Turning now to FIG. 5, a method 200 for forming a device or component (e.g., a valve) for a wearable drug delivery system is shown. At block 201, the method 200 may include providing a cylinder within a tube, the tube and the cylinder joined together in an interference fit. In some embodiments, an inside diameter of the cylinder, along an interior surface thereof, is less than an outside diameter of the tube, along an exterior surface thereof.

At block 203, the method 200 may include annealing the tube and the cylinder, wherein the tube and the cylinder are no longer joined together in the interference fit following the annealing. In some embodiments, the annealing process effectively resizes the tube and the cylinder such that after cooling, the cylinder and the tube are no longer in interference at an interface, and thus are able to move relative to one another with relatively lower force.

The foregoing discussion has been presented for purposes of illustration and description and is not intended to limit the disclosure to the form or forms disclosed herein. For example, various features of the disclosure may be grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the various methods disclosed herein are described as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes. Thus, the claims set forth below are to be construed in view of the full breadth and spirit of the present disclosure as described herein.

What is claimed is:

1. A method of forming a device for a wearable drug delivery system, the method comprising:
   joining together a first component within an interior of a second component, wherein the first and second components are engaged together in an interference fit;
   annealing the first and second components; and
   cooling the first and second components after the annealing until the first and second components are no longer engaged together in the interference fit.

2. The method of claim 1, further comprising pressing the second component over an exterior of the first component to cause the second component to expand.

3. The method of claim 1, wherein the first and second components are the same or different materials.

4. The method of claim 1, further comprising causing the first component to elongate after the annealing.

5. The method of claim 1, further comprising:
   providing a central port through the first component;
   providing an exterior port through the second component; and
   actuating the first and second components with respect to one another to align the central port with the exterior port.

6. The method of claim 1, wherein actuating the first and second components comprises rotating the first and second components with respect to one another or axially moving the first and second components with respect to one another.

7. A method of forming a valve for a medical device, comprising:
   providing a cylinder within a tube, the tube and the cylinder joined together in an interference fit such that an outer diameter of the cylinder is greater than an inner diameter of the tube;
   annealing the tube and the cylinder; and
   cooling the tube and the cylinder, wherein the tube and the cylinder are no longer joined together in the interference fit following the annealing and the cooling.

8. The method of claim 7, further comprising providing an oil between the tube and the cylinder.

9. The method of claim 7, further comprising pressing the tube over the cylinder to cause the cylinder to expand.

10. The method of claim 7, wherein the cylinder and the tube are the same material.

11. The method of claim 7, wherein the cylinder and the tube are different material.

12. The method of claim 7, further comprising causing the cylinder to elongate after the annealing.

13. The method of claim 7, further comprising providing a port through the tube or the cylinder.

14. The method of claim 7, further comprising:
   providing a central port through the cylinder;
   providing an exterior port through the tube; and
   actuating the tube and the cylinder with respect to one another to align the central port with the exterior port.

15. A method of forming a valve for a wearable medical device, comprising:
   providing a cylinder within a tube, the tube and the cylinder joined together in an interference fit;
   annealing the tube and the cylinder; and
   cooling the tube and the cylinder after the annealing until the cylinder and the tube are no longer engaged in the interference fit.

16. The method of claim 15, further comprising providing an oil between the tube and the cylinder.

17. The method of claim 15, wherein providing the cylinder within the tube comprises pressing the tube over the cylinder to cause the tube to expand.

18. The method of claim 15, wherein the cylinder and the tube are the same or different materials.

19. The method of claim 15, further comprising causing the cylinder to elongate after the annealing.

20. The method of claim 15, further comprising:
   providing a central port through the cylinder;
   providing an exterior port through the tube; and
   actuating the tube and the cylinder with respect to one another to align the central port with the exterior port.

* * * * *